United States Patent [19]

Beregi et al.

[11] 4,042,598
[45] Aug. 16, 1977

[54] DISUBSTITUTED AZABICYCLOALKANES

[75] Inventors: Laszlo Beregi, Boulogne; Pierre Hugon, Rueil-Malmaison; Xavier Pascaud, Paris; Jean-Claude Poignant, Bures, Yvette, all of France

[73] Assignee: Science Union et Cie, Societe Francaise de Recherche Medicale, Suresnes, France

[21] Appl. No.: 685,757

[22] Filed: May 13, 1976

Related U.S. Application Data

[62] Division of Ser. No. 525,623, Nov. 20, 1974, Pat. No. 3,972,994.

[30] Foreign Application Priority Data

Dec. 14, 1973 United Kingdom .............. 58034/73

[51] Int. Cl.² ........................................... C07D 209/44
[52] U.S. Cl. ................................................. 260/326.1
[58] Field of Search ...................................... 260/326.1

[56] References Cited
FOREIGN PATENT DOCUMENTS 1,229,653  4/1971  United Kingdom ............. 260/326.1

*Primary Examiner*—Ethel G. Love
*Attorney, Agent, or Firm*—Gordon W. Hueschen

[57] ABSTRACT

Disubstituted azabicycloalkanes of the formula

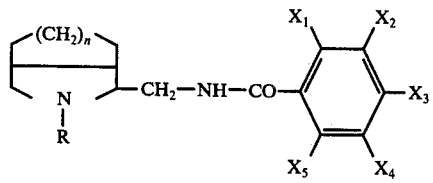

wherein:
  $n$ is 0, 1 or 2
  R is saturated or unsaturated straight or branched ($C_1$-$C_5$) aliphatic hydrocarbon, and
  $X_1$, $X_2$, $X_3$, $X_4$, $X_5$, which are the same or different, are hydrogen, halogen, hydroxy, lower alkyl, lower alkoxy, trifluoromethyl, nitro, amino or sulfamoyl.

These compounds are used as medicine especially in the treatment of gastroduodenal ulcers, gastric hypersecretion, nauseous syndromes of central origin and hypertension.

2 Claims, No Drawings

DISUBSTITUTED AZABICYCLOALKANES

This is a division of application Ser. No. 525,623, filed Nov. 20, 1974, now U.S. Pat. No. 3,972,994, issued Aug. 3, 1976.

The present invention provides disubstituted azabicycloalkanes of the general formula I:

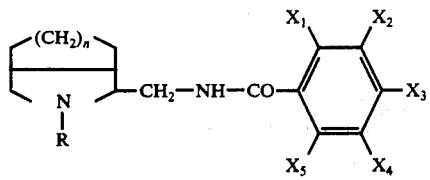

wherein:
  $n$ is selected from 0, 1 and 2;
  R is selected from the group consisting of saturated and unsaturated aliphatic hydrocarbon radical having from 1 to 5 carbon atoms inclusive in straight and branched chain and,
  $X_1$, $X_2$, $X_3$, $X_4$, and $X_5$, which are the same or different, are each selected from the group consisting of a hydrogen atom, halogen atoms, a hydroxy radical, alkyl and alkoxy radicals, each having from 1 to 5 carbon atoms inclusive, trifluoromethyl, nitro, amino and sulfamoyl radicals.

As aliphatic hydrocarbon radicals, cited for the meaning of R, there may be mentioned, for example, methyl, ethyl, propyl, butyl, allyl, methylpropenyl and butenyl radicals.

In the meaning of $X_1$, $X_2$, $X_3$, $X_4$ and $X_5$, there may be mentioned, for example, as halogen atoms : fluorine, chlorine and bromine atoms, as lower alkyl radicals : methyl, ethyl and propyl radicals, and as lower alkoxy radicals : methoxy, ethoxy and propoxy radicals.

Though all the compounds of the present invention possess valuable pharmacological properties, the compounds of the general formula I, wherein n is selected from 1 and 2, R is selected from ethyl and allyl and the phenyl nucleus of the benzamido moiety is mono-, di-or trisubstituted, are particularly interesting and, for these compounds, the preferred meanings for the X substituents are halogen, alkoxy, amino and sulfamoyl.

The present invention also provides acid addition salts, especially physiologically tolerable acid addtion salts, of compounds of the general formula I with the mineral and organic acids. As acid which may be used for the formation of these salts, there may be mentioned, for example, in the mineral series : hydrochloric, hydrobromic, sulfuric and phosphoric acids, and in the organic series : acetic, propionic, maleic, fumaric, tartaric, citric, oxalic, benzoic and methanesulfonic acids.

The compounds of the general formula I are new and were prepared according to the following processes which are included in the present invention.

The present invention provides a process for preparing a compound of the general formula I which comprises :

treating an azabicycloalkanone of the general formula II :

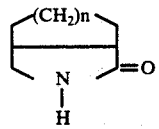

-continued

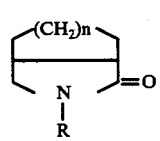

with an halide of the general formula III

Hal - R    III wherein
  Hal represents a halogen atom, in the presence of sodium hydride;
  treating the so-obtained compound of the general formula IV

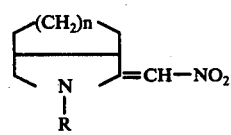

respectively with dimethyl sulfate, sodium methylate and nitromethane.

reducing the so-formed nitro compound of the general formula V

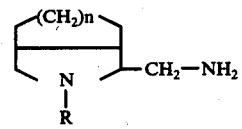

in the presence of Raney Nickel or lithium aluminium hydride
  then condensing the resulting -aminomethyl- azabicycloalkane of the general formula VI

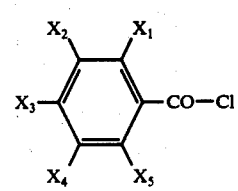

with the substituted benzoyl chloride of the general formula VII

$n$, R, $X_1$, $X_2$, $X_3$, $X_4$, and $X_5$ having in these formulae the same meanings as in formula I.

The reaction of compounds II and III in the presence of sodium hydride is suitably carried out in an anhydrous hydrocarbon such, for example, as xylene.

The reduction of the compound V is easily performed under a hydrogen pressure of about 5 kg/m2, in the presence of Raney nickel or lithium aluminium hydride in an anhydrous alcohol such, for example, as methanol.

The condensation of compounds VI et VII is carried out in an anydrous solvent such, for example, as tetrahydrofuran in the presence of an acceptor for the hydrochloric acid formed during the reaction, such, for example, as triethylamine.

The compounds of the general formula IV, V and VI are new and are included in the present invention together with the above mentioned process for preparing them. These compounds IV, V and VI are useful intermediates for the synthesis of compounds of the formula I.

The present invention also provides a process for preparing a compound of the general formula I wherein at least one of the substituents $X_1$, $X_2$, $X_3$, $X_4$ and $X_5$ is an amino group, which comprises condensing the here above defined -aminomethyl-azabicycloalkane of the general formula VI with an acetylamino benzoic acid of the general formula VIII

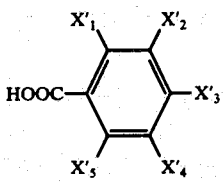

wherein at least one of the substituents $X'_1$, $X'_2$, $X'_3$, $X'_4$ and $X'_5$ is an acetylamino radical and the others have the same meanings as $X_1$, $X_2$, $X_3$, $X_4$, and $X_5$ excepted the value amino, then deacetylating the so-obtained compound of the general formula IX

IX

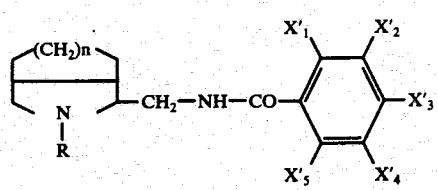

wherein n, R, $X'_1$, $X'_2$, $X'_3$, $X'_4$ and $X'_5$ are as defined above.

Such a deacetylation is easily carried out by heating the compound IX with an hydro alcoholic solution of sodium hydroxide.

The compounds of the general formula I and physiologically tolerable acid addition salts thereof, possess valuable pharmacological and therapeutic properties, especially antiemetic, gastric evacuation stimulating, gastric antisecretory, central nervous system depressing and hypotensive properties.

Their toxicity is low and their $LD_{50}$ determined in fasting mice varies from 60 to 750 mg/kg by intraperitoneal route.

The antiemetic activity was evidenced in the dog by the determination of the dose which inhibits the vomiting provoked by a subcutaneous injection of 100 μg/kg of apomorphine. It was demonstrated that the antiemetic activity of the compounds of the present invention, observed as well by oral route as by injectable route, is higher than the one of Sulpiride.

It was also observed that the compounds of the present invention possess a stimulating activity on the gastric evacuation; this property was studied by D. A. Brodie and S. K. Kundratz'technic (Fed. Proc. 25, 714,1965) by measuring the evacuation rate of pellets of amberlite calibrated to 1 mm, which was introduced by intubation in fasting rats, the day before the test. By subcutaneous route, the products of the invention show an average effective dose ($ED_{50}$) lower than those of the best product of reference.

The inhibiting activity on the gastric secretions was evidenced in rats, for the compounds of the present invention, according to the method of H. G. Shay et al. (gastroent. 5, 43,1945); there was observed a decrease of 40 to 60% of the output of acidity, 4 hours after the ligation of pylorus, at the doses ranged from 20 to 30 mg/kg by intraperitoneal and intraduodenal routes.

The neurological examination of mice and rats treated with the compounds of the present invention shows a decrease of the motility together with a notable decrease of conditioned reflexes in Skinner box.

Furthermore, an hypotensive activity in the anesthetized dog was found for the compounds of the present invention owed to their adrenolytic property.

The low toxicity and the above described pharmacological properties enable the use of the compounds of the present invention in therapy, especially in the treatment of gastroduodenal ulcers, gastric hypersecretion, nauseous syndromes of central origin and hypertension.

The present invention also provides a pharmaceutical preparation which contains a compound of the general formula I or a physiologically tolerable salt thereof in admixture or conjunction with a pharmaceutically suitable carrier such, for example, as distilled water, talc, starch, glucose or cocoa butter.

The so-obtained pharmaceutical preparations are advantageously in unit dosage form and may contain from 10 to 200 mg, preferably from 20 to 100 mg, of the active ingredient.

These pharmaceutical preparations may be in form of tablets, dragees, capsules, suppositories or injectable or drinkable solutions and may be administered by oral, rectal or parenteral route at a dose of from 10 to 200 mg, preferably from 20 to 100 mg in active ingredient, 1 to 5 times a day.

The following examples illustrate the invention, the parts being by weigh and the melting points being determined on a Kofler hot plate.

EXAMPLE 1

N-ethyl-2-(2-methoxy-5-sulfamoyl benzamido methyl)-3-azabicyclo (3,3,0) octane

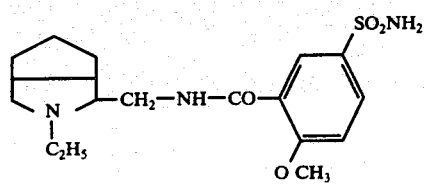

57.6 parts of sodium hydride at 50% (1.2 mole) in paraffine were introduced in 1500 parts of anhydrous xylene. To this suspension there was added portionwise in the course of 1 hour at room temperature, a solution of 150 parts (1.2 mole) of 3-azabicyclo (3,3,0)-2-octanone in 600 parts of anhydrous xylene. The mixture was refluxed for 45 minutes. After cooling, 187 parts (1.2 mole) of ethyl iodide were added in 30 minutes, then the reaction mixture was heated for 1 hour at 110° C. After cooling, 400 parts of water were added. The organic layer separated and dried over anhydrous magnesium sulfate was concentrated in vacuo. Upon distillation, there were obtained 95,5 parts of N-ethyl-3-azabicyclo (3,3,0)-2-octanone B.P./0.2 mmHg = 76°–79° C $n_D^{25}$ = 1.4872.

After extraction of the aqueous layer with 500 parts of chloroform, followed by drying concentration, the distillation gave another 46 parts of N-ethyl-3-azabicyclo (3,3,0)-2-octanone, having the same B.P. and $n_D^{25}$ than the product obtained from the organic layer.

74.7 parts (0,59 mole) of dimethyl sulfate were added in 20 minutes to 91 parts of N-ethyl-3-azabicyclo (3,3,0)- parts of concentrated HCl, the precipitated acid was filtered off, washed with water and finally dried. There were obtained 26.8 parts of 2-methoxy-5-sulfamoyl benzoic acid, M.P. 224°–225° C.

To a suspension of the so-obtained 2-methoxy-5-sulfamoyl benzoic acid in 600 parts of anhydrous tetrahydrofuran, there were added rapidly 27.5 parts of thionyl chloride. The mixture was refluxed for 2 hours. The solution was then evaporated under vacuo. The residue was treated with 500 parts of anhydrous benzene. After elimination of benzene in vacuo, there were obtained 29 parts of 2-methoxy-5-sulfamoyl benzoyl chloride, M.P.

was prepared starting from N-allyl-7-nitromethylene-8-azabicyclo (4,3,0) nonane, itself prepared starting from N-allyl-8-azabicyclo (4,3,0)-7-nonanone, obtained from 8-azabicyclo (4,3,0)-7-nonanone.

8. N-(2-methyl-2-propenyl)-2-(2-methoxy-5-sulfamoyl benzamido methyl)-3-azabicyclo (3,3,0) octane, M.P. 183°–185° C (ethanol), starting from 2-methoxy-5-sulfamoyl benzoyl chloride and N-(2-methyl-2 propenyl)-2-aminomethyl-3-azabicyclo (3,3,0) octane, B.P./0.1mm Hg :75°–77° C. This latter was prepared starting from N-(2-methyl-2-propenyl)-2-nitromethylene-3-azabicyclo (3,3,0) octane, M.P. 128°–129° C (isopropanol) itself prepared starting from N-(2-methyl-2-propenyl)-3-azabicyclo (3,3,0)-2-octanone, B.P. 0.3 mm Hg : 100°–102° C, obtained from 3-azabicyclo (3,3,0)-2-octanone.

9. N-ethyl-2-(2-methoxybenzamido methyl)-3-azabicyclo (3,3,0) octane, M.P. of its hydrochloride : 137°–138° C (ethyl acetate/isopropanol), starting from 2-methoxy benzoyl chloride and N-ethyl-2-aminomethyl-3-azabicyclo (3,3,0) octane.

10. N-ethyl-2-(3-trifluoromethyl benzamidomethyl)-3-azabicyclo (3,3,o) octane, M.P. 101° C (cyclohexane) starting from 3-trifluoromethylbenzoyl chloride and N-ethyl-2-aminomethyl-3-azabicyclo (3,3,0) octane.

11. N-ethyl-2-(2-methyl benzamido methyl)-3-azabicyclo (3,3,0) octane, M.P. 94° C (cyclohexane), starting from 2-methyl benzoyl chloride and N-ethyl-2-aminomethyl-3-azabicyclo (3,3,0) octane.

12. N-ethyl-2-(2-nitrobenzamido methyl)-3-azabicyclo (3,3,0) octane, M.P. 133° C (isopropanol), starting from 2-nitro benzoyl chloride and N-ethyl-2-aminomethyl-3-azabicyclo (3,3,0) octane.

13. N-ethyl-2-(2-amino benzamido methyl)-3-azabicyclo (3,3,0) octane, M.P. 115° C (cyclohexane), starting from 2-amino benzoyl chloride and N-ethyl-2-aminomethyl-3-azabicyclo (3,3,0) octane.

14. N-ethyl-2-(4-sulfamoyl benzamido methyl)-3-azabicyclo (3,3,0) octane, M.P. 235°–236° C (isopropanol), starting from 4-sulfamoyl benzoyl chloride and N-ethyl-2-aminomethyl-3-azabicyclo (3,3,0) octane.

15. N-ethyl-2-(3-sulfamoyl benzamido methyl)-3-azabicyclo (3,3,0) octane, M.P. 110° C (ethyl acetate), starting from 3-sulfamoyl benzoyl chloride and N-ethyl-2-aminomethyl-3-azabicyclo (3,3,0) octane.

16. N-ethyl-2-(4-fluoro benzamido methyl)-3-azabicyclo (3,3,0) octane, M.P. 112°–113° C (isopropanol/water), starting from 4-fluorobenzoyl chloride and N-ethyl-2-aminomethyl-3-azabicyclo (3,3,0) octane.

17. N-ethyl-2-(2-hydroxy benzamido methyl)-3-azabicyclo (3,3,0) octane, B.P. /0,1mmHg 175°–178° C, starting from 2-hydroxybenzoyl chloride and N-ethyl-2-amino methyl-3-azabicyclo (3,3,0) octane.

18. N-ethyl-7-(3-sulfamoyl-4-chloro benzamido methyl)-8-azabicyclo (4,3,0) nonane, M.P. of its hydrochloride : 262°–264° C (acetic acid), starting from 3-sulfamoyl-4-chloro benzoyl chloride and N-ethyl-7-aminomethyl-8-azabicyclo (4,3,0) nonane.

19. N-ethyl-7(methoxy-5-chloro benzamido methyl)-8-azabicyclo (4,3,0) nonane, M.P. of its hydrochloride : 170°–174° C (isopropanol), starting from 2-methoxy-5-chloro benzoyl chloride and N-ethyl-7-aminomethyl-8-azabicyclo (4,3,0) nonane.

EXAMPLE 20

N-ethyl-2-(2-methoxy-4-amino-5-chloro benzamido methyl)-3-azabicyclo (3,3,0) octane

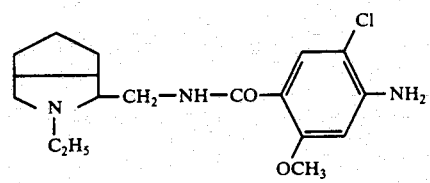

To a suspension of 6 parts of 2-methoxy-4-acetylamino-5-chloro benzoic acid in 50 parts of anhydrous tetrahydrofuran, were added 2.5 parts of triethylamine. The solution thus obtained was poured portionwise in a mixture of 2.7 parts of ethyl chloroformate in 80 parts of tetrahydrofuran maintained at 0° C. After stirring for 10 minutes, 4.1. parts of N-ethyl-2-aminomethyl-3-azabicyclo (3,3,0) octane were added. After being maintained at room temperature for 10 minutes, the temperature was progressively increased and, finally, the reaction mixture was refluxed for 60 minutes. After cooling, the mixture was filtered and the filtrate was evaporated in vacuo. After recrystallization in 50 parts of ethyl acetate, there were obtained 5.5. parts of N-ethyl-2-(2-methoxy-4-acetylamino-5-chloro benzamido methyl)-3-azabicyclo (3,3,0) octane, M.P. 156°–157° C (ethyl acetate).

7 parts of N-ethyl-2-(2-methoxy-4-acetylamino-5-chloro benzamido methyl)-3-azabicyclo (3,3,0) octane were heated for 30 minutes in the presence of 17.7 parts of a 2N solution of sodium hydroxide and 15 parts of ethanol. After cooling, the precipitate was filtered and recrystallized in 40 parts of acetonitrile. There were obtained 5 parts of N-ethyl-2-(2-methoxy-4-amino-5-chloro benzamido methyl)-3-azabicyclo (3,3,0) octane, M.P. 128°–129° C.

EXAMPLES 21 - 22

The following compounds were prepared according to the process described in Example 20.

21. N-ethyl-7-(2-methoxy-4-amino-5-chloro benzamido methyl)-8-azabicyclo (4,3,0) nonane, M.P. 165° C (isopropanol) starting from 2-methoxy-4-azetylamino-5-chloro benzoic acid and N-ethyl-7-aminomethyl-8-azabicyclo (4,3,0) nonane.

22. N-allyl-2-(2-methoxy-4-amino-5-chloro benzamido methyl)-3-azabicyclo (3,3,0) octane, M.P. 115° C (acetonitrile) starting from 2-methoxy-4-acetyl amino-5-chloro benzoic acid and N-allyl-2-aminomethyl-3-azabicyclo (3,3,0) octane.

We claim:

1. A compound selected from the group consisting of bicycloalkanes derivatives of the formula:

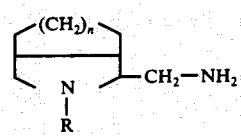

wherein n is 2, amd wherein R is selected from the group consisting of saturated and unsaturated aliphatic hydrocarbon radicals having 1 to 5 carbon atoms inclusive in the form of a straight or branched chain.

2. A compound of claim 1 which is N-ethyl-7-aminomethyl-8-azabicyclo (4,3,0) nonane.

* * * * *